(12) United States Patent
Urakawa et al.

(10) Patent No.: US 6,342,047 B1
(45) Date of Patent: Jan. 29, 2002

(54) INDWELLING CATHETER

(75) Inventors: Ryuichi Urakawa; Kazuyoshi Tani; Toru Kawashima; Akira Mochizuki, all of Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/323,951

(22) Filed: Jun. 2, 1999

(30) Foreign Application Priority Data

Jun. 2, 1998 (JP) ............................................. 10-152414
Jun. 2, 1998 (JP) ............................................. 10-152415

(51) Int. Cl.[7] .......................... A61M 5/00; C08F 283/00
(52) U.S. Cl. ........................................ 604/264; 525/458
(58) Field of Search ................................. 604/264, 523; 525/458; 428/36.8, 36.92, 35.7; 264/209.1

(56) References Cited

U.S. PATENT DOCUMENTS

| | | | |
|---|---|---|---|
| 5,061,254 A | | 10/1991 | Karakelle et al. |
| 5,102,401 A | * | 4/1992 | Lambert et al. ............ 604/264 |
| 5,120,816 A | | 6/1992 | Gould et al. |
| 5,159,051 A | * | 10/1992 | Onwumere et al. ........... 528/67 |
| 5,226,899 A | | 7/1993 | Lee et al. |
| 5,266,669 A | * | 11/1993 | Onwunaka et al. ........... 528/28 |
| 5,281,677 A | | 1/1994 | Onwunaka et al. |
| 5,334,691 A | | 8/1994 | Gould et al. |
| 5,453,099 A | | 9/1995 | Lee et al. |
| 5,458,935 A | * | 10/1995 | Alzner ....................... 428/35.7 |
| 5,545,708 A | | 8/1996 | Onwunaka et al. |
| 5,747,591 A | * | 5/1998 | Chen et al. ................. 525/176 |
| 5,814,705 A | * | 9/1998 | Ward et al. .................... 525/88 |
| 6,013,728 A | * | 1/2000 | Chen et al. ..................... 525/92 |

FOREIGN PATENT DOCUMENTS

| | | |
|---|---|---|
| EP | 0 586 132 A1 | 3/1994 |
| EP | 624 612 | 11/1994 |
| EP | 692 506 | 1/1996 |
| JP | 3-60672 | 3/1991 |
| JP | 8-11129 | 2/1996 |
| WO | 89/12653 | 12/1989 |
| WO | 98/21404 | 7/1996 |
| WO | 98/08884 | 3/1998 |

* cited by examiner

Primary Examiner—Sharon Kennedy
(74) Attorney, Agent, or Firm—Burns, Doane, Swecker & Mathis, L.L.P.

(57) ABSTRACT

An indwelling catheter is made of a blend of a plurality of polyurethane resins containing polyglycols having different molecular weights, or a polyurethane resin containing a plurality of polyglycols having different molecular weights. It shows a dynamic storage modulus of 1 GPa or more under a dry condition at 25° C. and decrease in dynamic storage modulus when changed from a dry condition at 25° C. to a wet condition at 37° C., a decrease percentage of the dynamic storage modulus being less than 60% at the elapsed time of 20 seconds and 60% or more at the elapsed time of 1 minute after placed under the wet condition at 37° C. Its Young's modulus is 50 kgf/mm$^2$ or more under a dry condition at 25° C., which reduces to 25 kgf/mm$^2$ or less within 5 minutes when placed under a wet condition at 37° C.

28 Claims, 4 Drawing Sheets

INDWELLING CATHETER

BACKGROUND OF THE INVENTION

The present invention relates to an indwelling catheter, more specifically to an indwelling catheter to be left in the blood vessel to perform infusion, introduction of a medical solution, blood transfusion, blood collection, monitor of blood circulation, etc.

An indwelling needle for infusion, transfusion, etc. has a plastic catheter tube capable of being left in place in the blood vessel with a distal end communicated with a tube extending from a receptacle, such as a infusion bag, containing a fluid, medicinal solution, blood, etc. A type of the indwelling needle has an integral structure through which a sharp-tipped internal needle made of metals, etc. extends. This type of the indwelling needle is inserted into the blood vessel together with the internal needle, which is then withdrawn from the catheter to conduct infusion, transfusion, etc. in the same manner as above.

Since the lumen of the catheter inserted into the body must be maintained large enough to effectuate the infusion and introduction of a medicinal solution, which are primary objectives of the indwelling needle, the catheter is required to have a high kink resistance. Further, the catheter is required to have sufficient stiffness for the insertion into the blood vessel and to soften after being left in the blood vessel, etc., because the mechanical properties of the catheter largely affect the puncture of the skin, the insertion of the catheter into the blood vessel and the indwelling of the catheter.

The conventional indwelling catheters are mainly made of fluoroplastics such as polytetrafluoroethylene, ethylene-tetrafluoroethylene copolymers, etc. Although the catheters made of fluoroplastics are sufficiently stiff for penetrating the skin and for insertion into the blood vessel, they do not sufficiently soften in contact with the blood. Therefore, the indwelling catheters made of fluoroplastics are likely to damage the inner wall of the blood vessel. Also, they are insufficient in kink resistance, posing the problems that they collapse in the blood vessel, preventing smooth flow of the infusion fluid.

In view of such circumstances, polyurethane resins having soft segments of polytetramethylene glycols have recently become widely used for the indwelling catheters. Japanese Patent Publication (JPB) 8-11129 discloses a catheter tube softening in the blood vessel, which is made of a hydrophilic polyetherurethane, the catheter tube having controlled balance between stiffness at the time of insertion and softness after being left in the blood vessel. However, the indwelling catheters made of polyetherurethanes are disadvantageous in failing to exhibit a sufficient kink resistance even after insertion into the blood vessel, although they become soft in contact with the blood. When the catheters are made stiffer for ease of insertion, their kink resistance is further deteriorated.

The catheters made of polyurethane resins can be improved in change in Young's modulus and in kink resistance by controlling molecular weights of the soft segments of the polyurethane resins. However, when only a polyurethane resin comprising a soft segment constituted by a polyglycol having a molecular weight of 500–1500 is used, the resultant catheter has insufficient kink resistance or never recovers its original shape once kinked even if the kink resistance is sufficient, though it exhibits large change in Young's modulus when changed from a dry condition at 25° C. to a wet condition at 37° C. On the other hand, when only a polyurethane resin comprising a soft segment constituted by a polyglycol having a molecular weight of 1500–3000 is used, the resultant catheter fails to exhibit large change in Young's modulus when changed from a dry condition at 25° C. to a wet condition at 37° C., though its kink resistance is sufficient. Thus, polyurethane resins having soft segments of substantially a single molecular weight fail to satisfy both requirements of change in Young's modulus and kink resistance.

Japanese Patent 2,723,190 discloses an indwelling needle made of shape-memory resins. A catheter of this indwelling needle exhibits sufficient stiffness at the time of insertion into the blood vessel and becomes soft after being left in the blood vessel. However, because such change of stiffness occurs too rapidly, it may become soft during the operation of insertion, making the insertion operation difficult.

OBJECT AND SUMMARY OF THE INVENTION

An object of the present invention is, therefore, to provide an indwelling catheter exhibiting as high stiffness as the fluoroplastic catheters at the time of insertion into the blood vessel and becoming soft after being left in the blood vessel, while exhibiting modulus decrease behavior suitable for indwelling operations and sufficient kink resistance.

As a result of research in view of the above object, the inventors have paid attention to the fact that it is important to control the speed of decrease in Young's modulus when changed from a dry condition at 25° C. to a wet condition at 37° C. in order that the indwelling catheter exhibits good stiffness (operability) at the time of insertion and becomes soft after inserted into the blood vessel, thereby avoiding the blood vessel from being damaged, that when the speed of decrease in Young's modulus is too slow, it takes too much time until the indwelling catheter becomes soft, thereby being likely to cause damage to the blood vessel after indwelled, and that when the Young's modulus of the indwelling catheter decreases too rapidly, the indwelling catheter becomes soft during the operation of insertion, thereby making the operation difficult.

What has been found as a result of investigation of the softening behavior of the polyurethane resins based on such findings is generally that how the polyurethane resins soften mostly depends upon the crystallinity of polyglycols contained in the polyurethane resins. When low-molecular weight polyglycols are contained in the polyurethane resins, the polyurethane resins are less likely to have large crystallinity, thus being accelerated in crystalline melting. As a result, the polyurethane resins exhibit an increased softening speed as temperature rises.

Because polymers having similar molecular structures generally have good compatibility, an additivity rule may be applicable to their blends. Accordingly, it may be expected that if a plurality of polyurethane resins having soft segments with different molecular weights were blended, or if a polyurethane resin were composed of a hard segment and a soft segment which is formed from a plurality of polyglycols having different molecular weights, their averaged properties would be obtained. However, the inventors have found that the additivity rule does not apply to the properties of such polyurethane resins as materials for the indwelling catheters. As a result of research, the inventors have found that when an indwelling catheter is made of a blend produced by combining a plurality of polyurethane resins each having poor properties, or when an indwelling catheter is made of a polyurethane resin produced by combining a plurality of polyglycols each forming a polyurethane resin with poor properties, the resultant indwelling catheter not only exhibits substantially the same stiffness as the fluoroplastic catheters at the time of insertion into the blood vessel and becomes soft after being left in the blood vessel, thereby avoiding the blood vessel from being damaged and showing decrease in Young's modulus suitable for the operation of indwelling, but also has excellent kink resistance. The present invention is based on this finding.

Thus, the indwelling catheter according to the present invention has a dynamic storage modulus of 1 GPa or more under a dry condition at 25° C. and showing decrease in dynamic storage modulus when changed from a dry condition at 25° C. to a wet condition at 37° C., a decrease percentage $E_p$ of the dynamic storage modulus, which is represented by the following equation:

$$E_p = [(E_0 - E_t)/(E_0 - E_{30})] \times 100\%,$$

wherein $E_0$ is a dynamic storage modulus under the dry condition at 25° C., $E_{30}$ is a dynamic storage modulus at the elapsed time of 30 minutes after placed under the wet condition at 37° C., and $E_t$ is a dynamic storage modulus at the elapsed time of t after placed under the wet condition at 37° C., being less than 60% at the elapsed time of 20 seconds after placed under the wet condition at 37° C. and 60% or more at the elapsed time of 1 minute after placed under the wet condition at 37° C.

The first example of the indwelling catheter exhibiting such decrease percentage of dynamic storage modulus is formed from a blend of a plurality of polyurethane resins containing polyglycols having different molecular weights. Each polyurethane resin preferably comprises a diisocyanate, a diol chain extender and polyglycols, the polyglycols having different molecular weights. A plurality of polyurethane resins preferably comprise a first polyurethane resin containing 20–70 weight % of polyglycol having a molecular weight of 500–1500 and a second polyurethane resin containing 20–70 weight % of polyglycol having a molecular weight of 1500–3000, the difference in molecular weight between the polyglycol in the first polyurethane resin and the polyglycol in the second polyurethane resin being 500 or more. Each of the polyurethane resins is preferably a reaction product of 4,4'-diphenylmethane diisocyanate, 1,4-butanediol and polycaprolactone glycol and has a Shore hardness of 60 D or more.

The second example of the indwelling catheter exhibiting a similar decrease percentage of dynamic storage modulus is made of a polyurethane resin containing a plurality of polyglycols having different molecular weights. The polyglycols contained in the polyurethane resin may be the same as described above, and other components constituting the polyurethane resin may also be the same as described above. The polyurethane resin preferably has a Shore hardness of 60 D or more.

The indwelling catheter according to a preferred embodiment of the present invention has a kink resistance of 10 mm or more both under a dry condition at 25° C. and a wet condition at 37° C. It also has a Young's modulus of 50 kgf/mm$^2$ or more under a dry condition at 25° C., which reduces to 25 kgf/mm$^2$ or less within 5 minutes when placed under a wet condition at 37° C.

DETAILED DESCRIPTION OF THE PREFERRED EMBODIMENTS

[1] Polyurethane Resins

Figure 1:
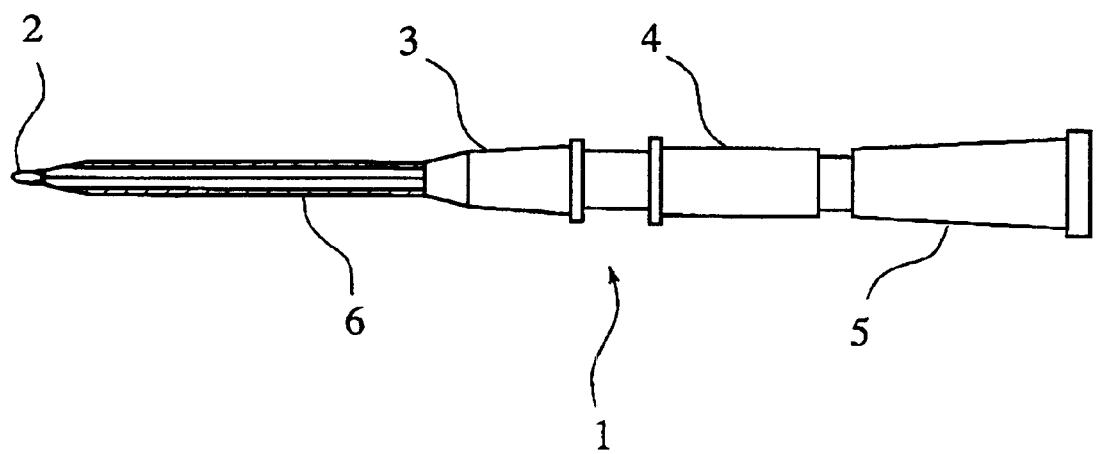
FIG. 1 is a schematic view showing the indwelling needle of the present invention.

To achieve maximum softening when changed from a dry condition at 25° C. to a wet condition at 37° C., a blend of a plurality of polyurethane resins containing polyglycols having different molecular weights, or a polyurethane resin containing a plurality of polyglycols having different molecular weights is used. The term "molecular weight" used herein means a number-average molecular weight, and the polyglycol used in the present invention has a narrow molecular weight distribution.

(A) Blend

Among a plurality of polyurethane resins to be blended, at least one polyurethane resin preferably comprises polyglycol having a molecular weight of 1500 or less, preferably 500–1500. When the molecular weight of the polyglycol is less than 500, such polyurethane resin fails to exhibit desired properties as a segmented polyurethane resin.

However, when only a polyurethane resin comprising a soft segment constituted by a polyglycol having a molecular weight of 500–1500 is used, the resultant catheter has insufficient kink resistance or never recovers its original shape once kinked even if the kink resistance is sufficient, though it exhibits large change in Young's modulus when changed from a dry condition at 25° C. to a wet condition at 37° C. On the other hand, when only a polyurethane resin comprising a soft segment constituted by a polyglycol having a molecular weight of 1500–3000 is used, the resultant catheter fails to exhibit large change in Young's modulus when changed from a dry condition at 25° C. to a wet condition at 37° C., though its kink resistance is sufficient. Therefore, the second polyurethane resin to be blended with the first polyurethane resin containing polyglycol having a molecular weight of 500–1500 is a polyurethane resin containing polyglycol having a molecular weight of 1500–3000.

Properties of the polyurethane resin are greatly variable depending on a polyglycol content therein. When the polyglycol content is less than 20 weight %, the polyurethane resin containing polyglycol having a molecular weight of 500–1500 is extremely hard, exhibiting a poor kink resistance and low decrease percentage of Young's modulus when changed from a dry condition at 25° C. to a wet condition at 37° C. On the other hand, when the polyglycol content is more than 70 weight %, the polyurethane resin has too small Young's modulus under a dry condition at 25° C., failing to provide the catheter with sufficient strength. Accordingly, in the polyurethane resin containing polyglycol having a molecular weight of 500–1500, the polyglycol content is preferably 20–70 weight %, more preferably 35–50 weight %.

In the polyurethane resin containing polyglycol having a molecular weight of 1500–3000, it is extremely hard and shows only a small decrease percentage of Young's modulus when changed from a dry condition at 25° C. to a wet condition at 37° C., when the polyglycol content is less than 20 weight %. On the other hand, when the polyglycol content is more than 70 weight %, the polyurethane resin is too soft to provide an indwelling catheter formed therefrom with sufficient strength. Accordingly, in the polyurethane resin containing polyglycol having a molecular weight of 1500–3000, the content of polyglycol is preferably 20–70 weight %, more preferably 30–55 weight %.

The difference in molecular weight between polyglycols contained in a plurality of polyurethane resins is preferably 500 or more. When the difference in molecular weight is less than 500, sufficient effects of blending a plurality of polyurethane resins containing polyglycols having different molecular weights cannot be obtained. The more preferable difference in the molecular weight of polyglycols is 1000 or more.

A weight ratio of the first polyurethane resin to the second polyurethane resin is preferably from 8:2 to 2:8. When the weight ratio is outside this range, sufficient effects of blending a plurality of polyurethane resins containing polyglycols having different molecular weights cannot be obtained.

Polyglycols, which may be used in the present invention, include polycaprolactone glycol, polyadipate glycol, polyether glycol, polycarbonate glycol, etc. Each polyurethane resin may contain one polyglycol or a combination of a plurality of polyglycols. Polyglycols contained in a plurality of polyurethane resins do not have to be the same, though they are preferably the same from the viewpoint of compatibility. Particularly preferable polyglycol is polycaprolactone glycol.

Other main components (for hard segment of polyurethane resin) to be combined with polyglycol are a diisocyanate, a diol chain extender, etc.

Diisocyanates, which may be used in the present invention, include aromatic diisocyanates such as 4,4'-diphenylmethane diisocyanate, 2,4-toluene diisocyanate, etc.; aliphatic diisocyanates such as hexamethylene diisocyanate, etc.; and alicyclic diisocyanates such as isophorone diisocyanate. Among them, 4,4'-diphenylmethane diisocyanate is the most preferable.

The chain extenders, which may be used in the present invention, include low-molecular weight diols such as 1,4-butanediol, ethylene glycol, diethylene glycol, triethylene glycol, propylene glycol, 1,6-hexanediol, etc. A particularly preferred chain extender is 1,4-butanediol. Ethylene diamine, butylene diamine, hexamethylene diamine, etc. may also be used as the chain extender to partially introduce urea bonds into the polyurethane resins.

(B) Polyurethane Resin Containing a Plurality of Polyglycols

In the case of a single polyurethane resin containing a plurality of polyglycols, the polyglycols and other main components (diisocyanate and diol chain extender) may be the same as described in (A) above.

With respect to polyglycols, the first polyglycol constituting a polyurethane resin preferably has a molecular weight of 1500 or less, more preferably 500–1500. Also, the second polyglycol preferably has a molecular weight of 1500–3000. The difference in molecular weight between the first and second polyglycols is preferably 500 or more, more preferably 1000 or more. When there is only a small difference in molecular weight among a plurality of polyglycols, it is impossible to obtain sufficient effects of blending a plurality of polyglycols having different molecular weights. Further, a weight ratio of the first polyglycol to the second polyglycol is preferably from 8:2 to 2:8. When the weight ratio is outside this range, sufficient effects of blending a plurality of polyglycols having different molecular weights cannot be obtained.

Properties of the polyurethane resin are greatly variable depending on the contents of a plurality of polyglycols having different molecular weights. To achieve a Shore hardness of 60 D or more, the hard segment content is preferably at least 40 weight %. Also, when the hard segment content is more than 80 weight %, the polyurethane resin is too hard, failing to show enough softness. Thus, the bard segment content is preferably 40–80 weight %, more preferably 50–70 weight %.

[2] Properties of Indwelling Catheter

The indwelling catheter of the present invention has excellent dynamic storage modulus, its decrease percentage due to wetting, Young's modulus, kink resistance and/or Shore hardness, regardless of whether it is formed from a blend of a plurality of polyurethane resins or a single polyurethane resin containing a plurality of polyglycols. The detailed explanations of these properties will be given below.

(A) Dynamic Storage Modulus

The indwelling catheter of the present invention has a dynamic storage modulus of 1 GPa or more under a dry condition at 25° C., and a decrease percentage of dynamic storage modulus when changed from a dry condition at 25° C. to a wet condition at 37° C. is less than 60% at the elapsed time of 20 seconds and 60% or more at the elapsed time of 1 minute.

The dynamic storage modulus of the indwelling catheter is measured using a dynamic storage modulus-measuring apparatus capable of conducting underwater measurement (DVA-225, available from IT Keisoku-Seigyo K. K.). First, a sample is fixed to a clamp of the above apparatus and subjected to a dynamic storage modulus measurement at a frequency of 10 Hz under a dry condition at 25° C. for 5 minutes without introducing water into the apparatus. Next, warm water kept at 37° C. is circulated in the apparatus to measure the dynamic storage modulus with time. The dynamic storage modulus lowers simultaneously with the circulation of warm water at 37° C. and substantially levels off at the elapsed time of 30 minutes. Thus, assuming that decrease in dynamic storage modulus at the elapsed time of 30 minutes after changed from a dry condition at 25° C. to a wet condition at 37° C. is 100%, the decrease percentage $E_p$ of dynamic storage modulus at the elapsed time of t under a wet condition at 37° C. is calculated from the following equation:

$$E_p = [(E_0 - E_t)/(E_0 - E_{30})] \times 100\%,$$

wherein $E_0$ is a dynamic storage modulus under the dry condition at 25° C., $E_{30}$ is a dynamic storage modulus at the elapsed time of 30 minutes after placed under the wet condition at 37° C., and $E_t$ is a dynamic storage modulus at the elapsed time of t after placed under the wet condition at 37° C.

When the dynamic storage modulus under a dry condition at 25° C. is less than 1 GPa, the indwelling catheter shows insufficient strength, providing poor operability at the time of insertion. Also, when the decrease percentage of dynamic storage modulus at the elapsed time of 20 seconds after placed under a wet condition at 37° C. is 60% or more, the indwelling catheter softens too rapidly in a wet state, still providing poor operability of indwelling. On the other hand, when the decrease percentage of dynamic storage modulus at the elapsed time of 1 minute after placed under a wet condition at 37° C. is less than 60%, the indwelling catheter softens too slowly in a wet state, likely to damage the blood vessel walls. The decrease percentage of dynamic storage modulus after changed from a dry condition at 25° C. to a wet condition at 37° C. is preferably 55% or less at the elapsed time of 20 seconds and 65% or more at the elapsed time of 1 minute.

(B) Young's Modulus

The Young's modulus of 50 kgf/mm$^2$ or more under a dry condition at 25° C. is as high as that of the indwelling catheters made of fluoroplastics, satisfying the requirements of operability at the time of insertion. To prevent the blood vessel wall from being damaged by the catheter inserted, the Young's modulus of the indwelling catheter is preferably reduced to 25 kgf/mm$^2$ or less within 5 minutes after placed under a wet condition at 37° C. More preferably, the Young's modulus is 55 kgf/mm$^2$ or more under a dry condition at 25° C., and 20 kgf/mm$^2$ or less within 5 minutes after placed under a wet condition at 37° C. As described above, how the indwelling catheter softens from the time of insertion to indwelling in the blood vessel is important. In order to achieve the optimum softening, it is preferable that the Young's modulus decreases by 25 kgf/mm$^2$ or more, more preferably 35 kgf/mm$^2$ or more when changed from a dry condition at 25° C. to a wet condition at 37° C.

The measurement of Young's modulus is carried out as follows: First, a tensile test is conducted on a sample by a tensile tester (Strogaph T, manufactured by Toyo Seiki Seisakusho Co. Ltd.) under the conditions of a gage distance of 10 mm and a test speed of 5 mm/min. under a dry condition at 25° C. and a wet condition after soaking the indwelling catheter in warm water at 37° C. for a predetermined period of time. The Young's modulus is then determined from a straight-line portion of the tensile stress-strain curve thus obtained.

(C) Kink Resistance

The kink resistance of the indwelling catheter of the present invention is preferably 10 mm or more, more preferably 12 mm or more, most preferably 14 mm or more both under a dry condition at 25° C. and a wet condition at 37° C., to stably keep sufficient flow when the indwelling catheter is placed in the blood vessel.

Figure 2:
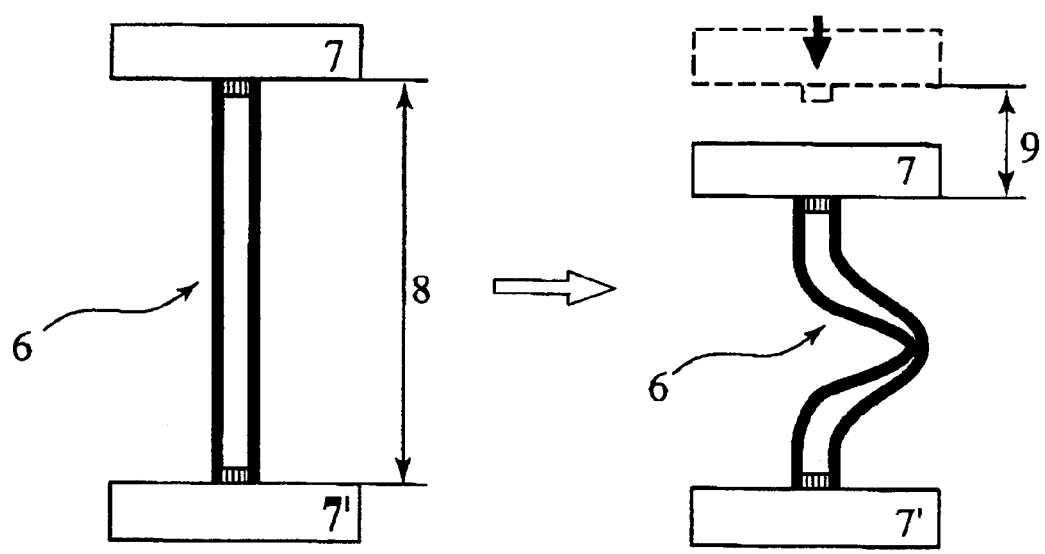
FIG. 2 is a schematic view illustrating a compression test machine A and a compression test method for measuring the kink resistance of indwelling catheters.

The kink resistance is measured using a compression tester (Autograph AGS-100A manufactured by Shimadzu Corporation, simply called "tester A") as shown in FIG. 2. The tester A comprises an upper clamp 7 movable up and down at a constant rate and a lower stationary clamp 7', and the clamps 7, 7' hold a catheter tube 6 cut to a predetermined length 8. The upper clamp 7 moves downward to apply a load axially to the catheter tube 6 to automatically record change in the load applied to the catheter tube 6 onto a chart as a function of the moving distance of the upper clamp 7.

With a sample length 8 of 25 mm and a moving rate of the upper clamp 7 kept constant at 50 mm/min, the catheter 6 is measured under a dry condition at 25° C., and then under a wet condition at 37° C. after soaking in warm water at 37° C. for a predetermined period of time.

Figure 3:
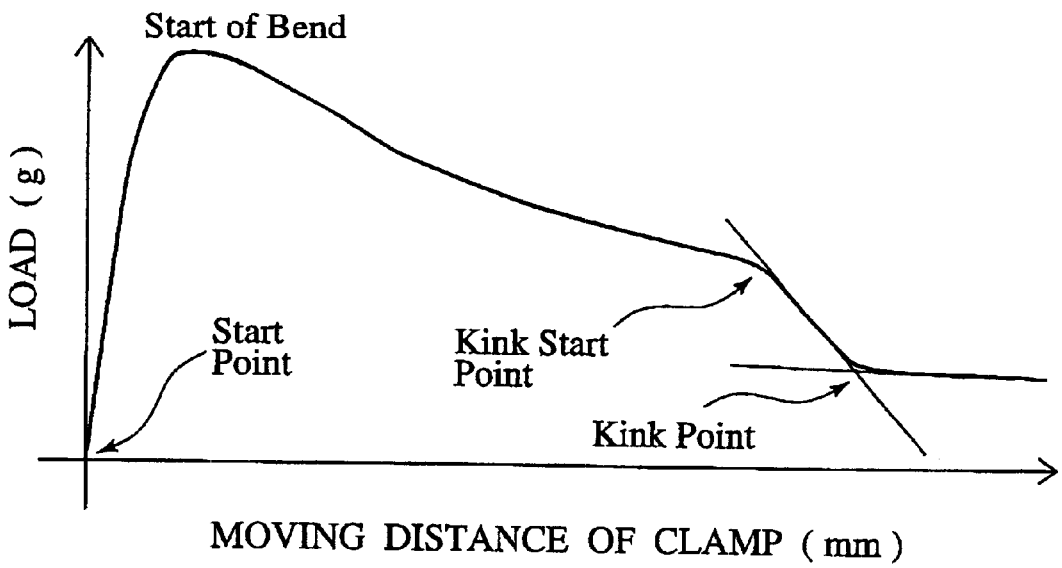
FIG. 3 is a graph showing the relation between a load applied to the catheter being measured and the moving distance of a clamp for holding a catheter sample, illustrating the kink resistance of the catheter.

As the catheter tube 6 is compressed by the upper clamp 7 moving downward as shown in FIG. 2, the load applied to the catheter tube 6 changes with the moving distance. As is clear from FIG. 3 showing change in the load, the load applied to the catheter tube 6 instantaneously increases and then gradually decreases when the catheter starts to bend (start of bend). Further compression of the catheter causes the catheter to collapse, closing the inside of the catheter. This phenomenon is called "kink." As soon as the kink starts, the load decreases drastically, thereby giving an inflection point (kink start point) to the load-moving distance curve. When the inner cavity of the catheter is almost closed, the load becomes nearly constant, giving another inflection point to the load-moving distance curve (kink point). The upper clamp 7 moves by a distance 9 (mm) from the start point of the compression test to the kink point at which the inside of the catheter is closed as shown in FIGS. 2 and 3. Thus, the kink resistance is represented by the distance 9 (mm).

(D) Shore Hardness

The polyurethane resin preferably has a Shore hardness of 60 D or more for ease of inserting the indwelling catheter into the blood vessel. When the Shore hardness is less than 60 D, good operation of insertion cannot be achieved due to insufficient stiffness. When the Shore hardness is larger than 85 D, however, the polyurethane resin cannot easily be extrusion-molded, thereby failing to provide an indwelling catheter with a desired shape. Practically preferable Shore hardness of the indwelling catheter is 65–80 D.

(E) Others

The indwelling catheter of the present invention may have at least one stripe of a polyurethane resin containing an X-ray-opaque agent as a visualizing aid for easily finding its position. Such stripe is effective particularly when the indwelling catheter is accidentally broken, leaving its fragments in the blood vessel. An indwelling catheter having a plurality of stripes may be easily formed by coextrusion of a polyurethane resin for a matrix of the catheter and a polyurethane resin for stripes containing the X-ray-opaque agent such as barium sulfate, tungsten, bismuth oxide, bismuth subcarbonate, gold, etc. The X-ray-opaque agents are not restricted to the above. The stripes can be formed in any shape and number by suitably selecting the design of the coextrusion die.

The present invention will be further explained in detail referring to EXAMPLES below, without intention to restrict the present invention thereto. Polyurethane resins used in EXAMPLES were prepared from a combination of various soft segment components with other components consisting of 4,4'-diphenylmethane diisocyanate (MDI) as a diisocyanate and 1,4-butanediol as a diol, at a molar ratio of [NCO]/[OH]=1 by a one-shot process or a prepolymer process. The term "other components" used in EXAMPLES means the above combination of MDI and 1,4-butanediol. Though EXAMPLES 1–9 refer to only polyglycols, it should be noted that the other components were added to polyglycols at the above molar ratio to provide polyurethane resins.

EXAMPLE 1

A polyurethane resin having a Shore hardness of 78 D and comprising 37 weight % of a soft segment made of polycaprolactone glycol having a molecular weight of 550 and a polyurethane resin having a Shore hardness of 68 D and comprising 42 weight % of a soft segment made of polycaprolactone glycol having a molecular weight of 2000 were melt-blended at a weight ratio of 6/4 to extrude a catheter 6 having an inner diameter of 0.65 mm and an outer diameter of 0.88 mm. This catheter 6 was fixed to a hub 3 with a caulking pin (not shown) such that an effective length of the catheter was 25 mm. An internal needle 2 fixed to one end of a needle hub 4 was coaxially inserted into the indwelling catheter 6. A filter cap 5 was finally disposed at the other end of the needle hub 4 to produce an indwelling needle 1 as shown in FIG. 1.

The catheter 6 used in this indwelling needle 1 was subjected to a tensile test by a tensile tester (Strograph T, manufactured by Toyo Seiki Seisakusho Co. Ltd.) in the same manner as described above, to determine Young's modulus both under a dry condition at 25° C. and under a wet condition after soaking in warm water at 37° C. for a prescribed period of time.

The kink resistance of this catheter was measured using the tester A shown in FIG. 2 in the same manner as described above both under a dry condition at 25° C. and under a wet condition after soaking in warm water at 37° C. for a prescribed period of time.

Figure 4:
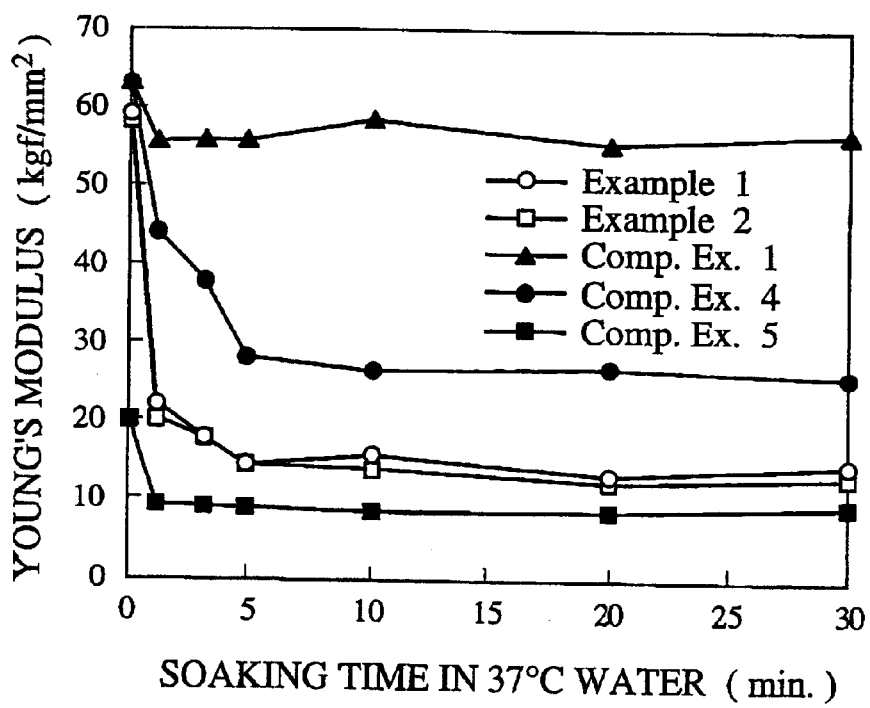
FIG. 4 is a graph showing the relation between Young's modulus and immersion time in warm water at 37° C. in EXAMPLES 1 and 2 and COMPARATIVE EXAMPLES 1, 4 and 5.
Figure 5:
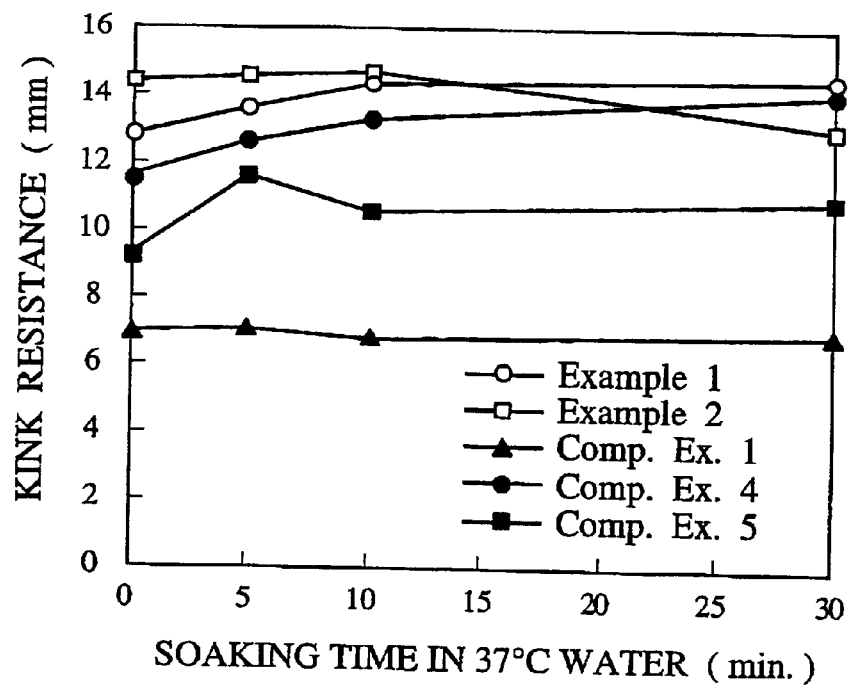
FIG. 5 is a graph showing the relation between kink resistance and immersion time in warm water at 37° C. in EXAMPLES 1 and 2 and COMPARATIVE EXAMPLES 1, 4 and 5.

The Young's modulus and kink resistance of this catheter are shown in FIGS. 4 and 5. The Young's modulus was 59 kgf/mm$^2$ under a dry condition at 25° C. (0 minute in FIG. 4), proving that this catheter had sufficient stiffness for insertion to the blood vessel. The catheter immediately became soft under a wet condition at 37° C., exhibiting Young's modulus of 14 kgf/mm$^2$ after 5 minutes. The kink resistance of this catheter was as good as 12.9 mm under a dry condition at 25° C. (0 minute in FIG. 5) and 14.2 mm at the elapsed time of 10 minutes after soaking in warm water at 37° C.

Next, the dynamic storage modulus of this catheter was measured according to the above-described method both under a dry condition at 25° C. and under a wet condition at 37° C. at the elapsed time of 20 seconds and 1 minute, respectively, and a decrease percentage of dynamic storage modulus at the elapsed time of 20 seconds and 1 minute, respectively, under a wet condition at 37° C. was determined. The results are shown in Table 1. The decrease percentage of dynamic storage modulus under a wet condition at 37° C. was 54% at the elapsed time of 20 seconds and 74% at the elapsed time of 1 minute, proving that this catheter exhibited satisfactory decrease in modulus.

EXAMPLE 2

A polyurethane resin having a Shore hardness of 70 D and comprising 46 weight % of a soft segment made of polycaprolactone glycol having a molecular weight of 550 and a polyurethane resin having a Shore hardness of 74 D and comprising 32 weight % of a soft segment made of polycaprolactone glycol having a molecular weight of 2000 were melt-blended at a weight ratio of 1/1 to extrude a catheter 6 having an inner diameter of 0.66 mm and an outer diameter of 0.89 mm. An indwelling needle 1 was produced with this catheter 6 in the same manner as in Example 1. Also, the catheter 6 was measured with respect to Young's modulus and kink resistance in the same manner as Example 1.

The Young's modulus and kink resistance of this catheter are shown in FIGS. 4 and 5. The Young's modulus was 58 kgf/mm$^2$ under a dry condition at 25° C., proving that this catheter had sufficient stiffness for insertion to the blood vessel. The catheter immediately became soft under a wet condition at 37° C., exhibiting Young's modulus of 14 kgf/mm$^2$ after 5 minutes. The kink resistance of this catheter was as good as 14.3 mm under a dry condition at 25° C. and 14.8 mm at the elapsed time of 10 minutes after soaking in warm water at 37° C.

EXAMPLE 3

A polyurethane resin having a Shore hardness of 76 D and comprising 32 weight % of a soft segment made of polycaprolactone glycol having a molecular weight of 1000 and a polyurethane resin having a Shore hardness of 70 D and comprising 37 weight % of a soft segment made of polycaprolactone glycol having a molecular weight of 2000 were melt-blended at a weight ratio of 1/1 to extrude a catheter 6 having an inner diameter of 0.65 mm and an outer diameter of 0.88 mm. An indwelling needle 1 was produced with this catheter 6 in the same manner as in Example 1. Also, the catheter 6 was measured with respect to Young's modulus and kink resistance in the same manner as Example 1.

The Young's modulus was as large as 58 kgf/mm$^2$ under a dry condition at 25° C., proving that this catheter had sufficient stiffness for insertion to the blood vessel. The catheter immediately became soft under a wet condition at 37° C., exhibiting Young's modulus of 20 kgf/mm$^2$ after 5 minutes. The kink resistance of this catheter was as good as 13.5 mm under a dry condition at 25° C. and 15.1 mm at the elapsed time of 10 minutes after soaking in warm water at 37° C.

EXAMPLE 4

A polyurethane resin having a Shore hardness of 78 D and comprising 37 weight % of a soft segment made of polycaprolactone glycol having a molecular weight of 550 and a polyurethane resin having a Shore hardness of 66 D and comprising 37 weight % of a soft segment made of polycaprolactone glycol having a molecular weight of 3000 were melt-blended at a weight ratio of 6/4 to extrude a indwelling catheter 6 having an inner diameter of 0.66 mm and an outer diameter of 0.88 mm. An indwelling needle 1 was produced with this catheter 6 in the same manner as in Example 1. Also, the catheter 6 was measured with respect to Young's modulus and kink resistance in the same manner as Example 1.

The Young's modulus was as large as 58 kgf/mm$^2$ under a dry condition at 25° C., proving that this catheter had sufficient stiffness for insertion to the blood vessel. The catheter immediately became soft under a wet condition at 37° C., exhibiting Young's modulus of 18 kgf/mm$^2$ after 5 minutes. The kink resistance of this catheter was as good as 11.8 mm under a dry condition at 25° C. and 16.2 mm at the elapsed time of 10 minutes after soaking in warm water at 37° C.

EXAMPLE 5

A polyurethane resin having a Shore hardness of 78 D and comprising 37 weight % of a soft segment made of polyhexamethylenecarbonate glycol having a molecular weight of 1000, and a polyurethane resin having a Shore hardness of 64 D and comprising 42 weight % of a soft segment made of polyhexamethylenecarbonate glycol having a molecular weight of 2000 were melt-blended at a weight ratio of 1/1 to extrude a catheter 6 having an inner diameter of 0.65 mm and an outer diameter of 0.89 mm. An indwelling needle 1 was produced with this catheter 6 in the same manner as in Example 1. Also, the catheter 6 was measured with respect to Young's modulus and kink resistance in the same manner as Example 1.

The Young's modulus was 58 kgf/mm$^2$ under a dry condition at 25° C., proving that this catheter had sufficient stiffness for insertion to the blood vessel. The catheter immediately became soft under a wet condition at 37° C., exhibiting Young's modulus of 21 kgf/mm$^2$ after 5 minutes. The kink resistance of this catheter was as good as 15.1 mm under a dry condition at 25° C. and 17.5 mm at the elapsed time of 10 minutes after soaking in warm water at 37° C.

Next, the dynamic storage modulus of this catheter 6 was measured according to the above-described method both under a dry condition at 25° C. and under a wet condition at 37° C. at the elapsed time of 20 seconds and 1 minute, respectively, and a decrease percentage of dynamic storage modulus at the elapsed time of 20 seconds and 1 minute, respectively, under a wet condition at 37° C. was determined. The results are shown in Table 1. The decrease percentage of dynamic storage modulus under a wet condition at 37° C. was 52% at the elapsed time of 20 seconds and 69% at the elapsed time of 1 minute, proving that this catheter exhibited satisfactory decrease in modulus.

EXAMPLE 6

A polyurethane resin having a Shore hardness of 79 D and comprising 32 weight % of a soft segment made of polytetramethylene glycol having a molecular weight of 650, and a polyurethane resin having a Shore hardness of 65 D and comprising 42 weight % of a soft segment made of polycaprolactone glycol having a molecular weight of 2000 were melt-blended at a weight ratio of 7/3 to extrude a catheter 6 having an inner diameter of 0.65 mm and an outer diameter of 0.88 mm. An indwelling needle 1 was produced with this catheter 6 in the same manner as in Example 1. Also, the catheter 6 was measured with respect to Young's modulus and kink resistance in the same manner as Example 1.

The Young's modulus was 60 kgf/mm$^2$ under a dry condition at 25° C., proving that this catheter had sufficient stiffness for insertion to the blood vessel. The catheter immediately became soft under a wet condition at 37° C., exhibiting Young's modulus of 16 kgf/mm$^2$ after 5 minutes. The kink resistance of this catheter was as good as 10.2 mm under a dry condition at 25° C. and 14.8 mm at the elapsed time of 10 minutes after soaking in warm water at 37° C.

EXAMPLE 7

A polyurethane resin having a Shore hardness of 78 D and comprising 37 weight % of a soft segment made of polyhexamethylenecarbonate glycol having a molecular weight of 1000, and a polyurethane resin having a Shore hardness of 65 D and comprising 42 weight % of a soft segment made of polycaprolactone glycol having a molecular weight of 2000 were melt-blended at a weight ratio of 6/4 to extrude a catheter 6 having an inner diameter of 0.67 mm and an outer diameter of 0.87 mm. An indwelling needle 1 was produced with this catheter 6 in the same manner as in Example 1. Also, the catheter 6 was measured with respect to Young's modulus and kink resistance in the same manner as Example 1.

The Young's modulus was 61 kgf/mm$^2$ under a dry condition at 25° C., proving that this catheter had sufficient stiffness for insertion to the blood vessel. The catheter immediately became soft under a wet condition at 37° C., exhibiting Young's modulus of 21 kgf/mm$^2$ after 5 minutes. The kink resistance of this catheter was 10.0 mm under a dry condition at 25° C. and 12.5 mm at the elapsed time of 10 minutes after soaking in warm water at 37° C.

EXAMPLE 8

A polyurethane resin having a Shore hardness of 79 D and comprising 32 weight % of a soft segment made of polytetramethylene glycol having a molecular weight of 650, and a polyurethane resin having a Shore hardness of 67 D and comprising 42 weight % of a soft segment made of polytetramethylene glycol having a molecular weight of 2000 were melt-blended at a weight ratio of 6/4 to extrude a catheter 6 having an inner diameter of 0.68 mm and an outer diameter of 0.86 mm. An indwelling needle 1 was produced with this catheter 6 in the same manner as in Example 1. Also, the catheter 6 was measured with respect to Young's modulus in the same manner as Example 1.

The Young's modulus was 67 kgf/mm$^2$ under a dry condition at 25° C., proving that this catheter had sufficient stiffness for insertion to the blood vessel. The catheter immediately became soft under a wet condition at 37° C., exhibiting Young's modulus of 20 kgf/mm$^2$ after 5 minutes.

EXAMPLE 9

A polyurethane resin having a Shore hardness of 79 D and comprising 32 weight % of a soft segment made of polytetramethylene glycol having a molecular weight of 650, and a polyurethane resin having a Shore hardness of 65 D and comprising 42 weight % of a soft segment made of polytetramethylene glycol having a molecular weight of 2000 were melt-blended at a weight ratio of 7/3 to extrude a catheter 6 having an inner diameter of 0.65 mm and an outer diameter of 0.88 mm.

The dynamic storage modulus of this catheter 6 was measured according to the above-described method both under a dry condition at 25° C. and under a wet condition at 37° C. at the elapsed time of 20 seconds and 1 minute, respectively, and a decrease percentage of dynamic storage modulus at the elapsed time of 20 seconds and 1 minute, respectively, under a wet condition at 37° C. was determined. The results are shown in Table 1. The decrease percentage of dynamic storage modulus under a wet condition at 37° C. was 45% at the elapsed time of 20 seconds and 69% at the elapsed time of 1 minute, proving that this catheter exhibited satisfactory decrease in modulus.

EXAMPLE 10

22.2 weight % of polycaprolactone glycol having a molecular weight of 550 and 16.6 weight % of polycaprolactone glycol having a molecular weight of 2000, based on the total ingredients (100 weight %), were mixed with the above other components to prepare a polyurethane resin having a Shore hardness of 78 D by a conventional method. The polyurethane resin was extruded to form a catheter 6 having an inner diameter of 0.66 mm and an outer diameter of 0.89 mm. An indwelling needle 1 was produced with this catheter 6 in the same manner as in Example 1. Also, the catheter 6 was measured with respect to Young's modulus and kink resistance in the same manner as Example 1.

Figure 6:
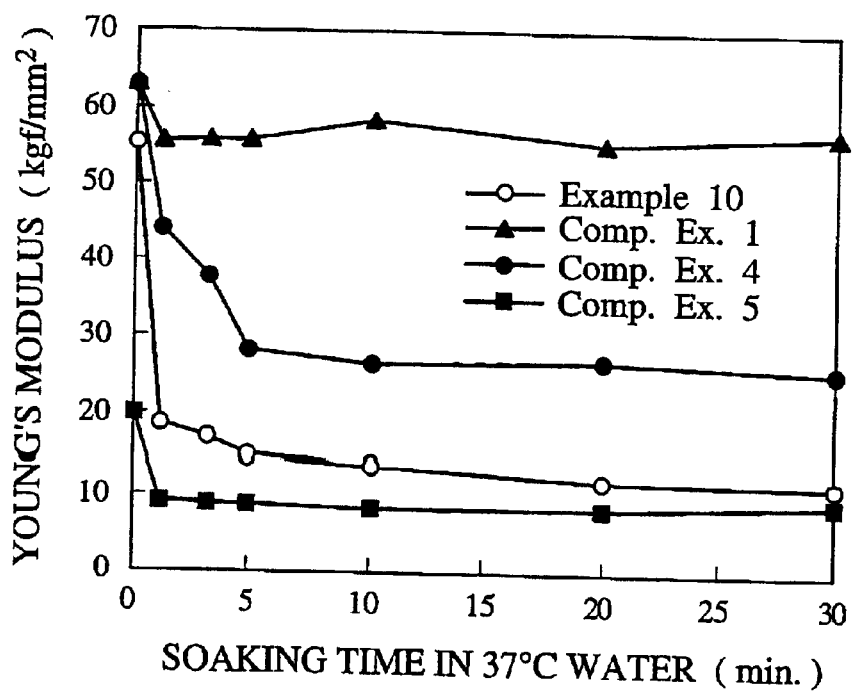
FIG. 6 is a graph showing the relation between Young's modulus and immersion time in warm water at 37° C. in EXAMPLE 10 and COMPARATIVE EXAMPLES 1, 4 and 5.
Figure 7:
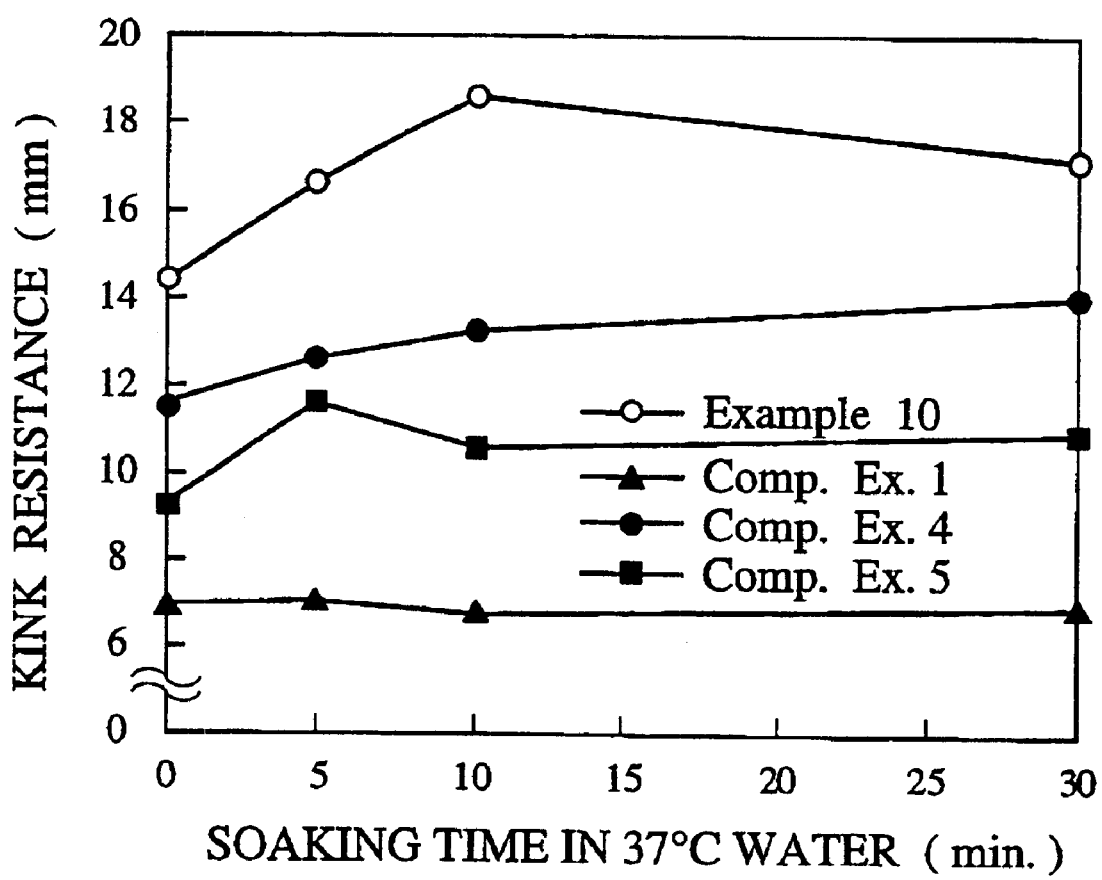
FIG. 7 is a graph showing the relation between kink resistance and immersion time in warm water at 37° C. in EXAMPLE 10 and COMPARATIVE EXAMPLES 1, 4 and 5.

The Young's modulus and kink resistance of this catheter are shown in FIGS. 6 and 7. FIGS. 6 and 7 also illustrate the Young's modulus and kink resistance of COMPARATIVE EXAMPLES 1, 4 and 5 for comparison.

The Young's modulus was 56 kgf/mm$^2$ under a dry condition at 25° C. (0 minute in FIG. 6), proving that this catheter had sufficient stiffness for insertion to the blood vessel. The catheter immediately became soft under a wet condition at 37° C., exhibiting Young's modulus of 15 kgf/mm$^2$ after 5 minutes. The kink resistance of this catheter was as good as 14.3 mm under a dry condition at 25° C. (0 minute in FIG. 7) and 18.4 mm at the elapsed time of 10 minutes after soaking in warm water at 37° C.

EXAMPLE 11

23 weight % of polycaprolactone glycol having a molecular weight of 550 and 16 weight % of polycaprolactone glycol having a molecular weight of 2000, based on the total ingredients (100 weight %), were mixed with the above other components to prepare a polyurethane resin having a Shore hardness of 77 D by a conventional method. The polyurethane resin was extruded to form a catheter 6 having an inner diameter of 0.65 mm and an outer diameter of 0.88 mm by a conventional method. An indwelling needle 1 was produced with this catheter 6 in the same manner as in Example 1. Also, the catheter 6 was measured with respect to Young's modulus and kink resistance in the same manner as Example 1.

The Young's modulus was 59 $kgf/mm^2$ under a dry condition at 25° C., proving that this catheter had sufficient stiffness for insertion to the blood vessel. The catheter immediately became soft under a wet condition at 37° C., exhibiting Young's modulus of 15 $kgf/mm^2$ after 5 minutes. The kink resistance of this catheter was as good as 14.1 mm under a dry condition at 25° C. and 14.7 mm at the elapsed time of 10 minutes after soaking in warm water at 37° C.

The dynamic storage modulus of this catheter was measured according to the above-described method both under a dry condition at 25° C. and under a wet condition at 37° C. at the elapsed time of 20 seconds and 1 minute, respectively, and a decrease percentage of dynamic storage modulus at the elapsed time of 20 seconds and 1 minute, respectively, under a wet condition at 37° C. was determined. The results are shown in Table 1. The dynamic storage modulus of this catheter was 1.3 GPa under a dry condition at 25° C., and the decrease percentage of dynamic storage modulus under a wet condition at 37° C. was 55% at the elapsed time of 20 seconds and 68% at the elapsed time of 1 minute, proving that this catheter exhibited satisfactory decrease in modulus.

EXAMPLE 12

16 weight % of polycaprolactone glycol having a molecular weight of 1000 and 13.5 weight % of polycaprolactone glycol having a molecular weight of 2000, based on the total ingredients (100 weight %), were mixed with the above other components to prepare a polyurethane resin having a Shore hardness of 77 D by a conventional method. The polyurethane resin was extruded to form a catheter 6 having an inner diameter of 0.64 mm and an outer diameter of 0.88 mm. An indwelling needle 1 was produced with this catheter 6 in the same manner as in Example 1. Also, the catheter 6 was measured with respect to Young's modulus and kink resistance in the same manner as Example 1.

The Young's modulus was 58 $kgf/mm^2$ under a dry condition at 25° C., proving that this catheter had sufficient stiffness for insertion to the blood vessel. The catheter immediately became soft under a wet condition at 37° C., exhibiting Young's modulus of 18 $kgf/mm^2$ after 5 minutes. The kink resistance of this catheter was as good as 13.2 mm under a dry condition at 25° C. and 14.8 mm at the elapsed time of 10 minutes after soaking in warm water at 37° C.

EXAMPLE 13

18.5 weight % of polyhexamethylenecarbonate glycol having a molecular weight of 1000 and 21 weight % of polyhexamethylenecarbonate glycol having a molecular weight of 2000, based on the total ingredients (100 weight %), were mixed with the above other components to prepare a polyurethane resin having a Shore hardness of 76 D by a conventional method. The polyurethane resin was extruded to form a catheter 6 having an inner diameter of 0.65 mm and an outer diameter of 0.89 mm. An indwelling needle 1 was produced with this catheter 6 in the same manner as in Example 1. Also, the catheter 6 was measured with respect to Young's modulus and kink resistance in the same manner as Example 1.

The Young's modulus was 58 $kgf/mm^2$ under a dry condition at 25° C., proving that this catheter had sufficient stiffness for insertion to the blood vessel. The catheter immediately became soft under a wet condition at 37° C., exhibiting Young's modulus of 20 $kgf/mm^2$ after 5 minutes. The kink resistance of this catheter was as good as 13.9 mm under a dry condition at 25° C. and 14.5 mm at the elapsed time of 10 minutes after soaking in warm water at 37° C.

EXAMPLE 14

19.2 weight % of polytetramethylene glycol having a molecular weight of 650 and 16.8 weight % of polytetramethylene glycol having a molecular weight of 2000, based on the total ingredients (100 weight %), were mixed with the above other components to prepare a polyurethane resin having a Shore hardness of 78 D by a conventional method. The polyurethane resin was extruded to form a catheter 6 having an inner diameter of 0.65 mm and an outer diameter of 0.87 mm. An indwelling needle 1 was produced with this catheter 6 in the same manner as in Example 1. Also, the catheter 6 was measured with respect to Young's modulus in the same manner as Example 1.

The Young's modulus was 65 $kgf/mm^2$ under a dry condition at 25° C., proving that this catheter had sufficient stiffness for insertion to the blood vessel. The catheter immediately became soft under a wet condition at 37° C., exhibiting Young's modulus of 21 $kgf/mm^2$ after 5 minutes.

Comparative Example 1

An ethylene-tetrafluoroethylene resin was extruded to form a catheter having an inner diameter of 0.64 mm and an outer diameter of 0.83 mm, which was then formed into an indwelling needle. The Young's modulus and kink resistance of this catheter are shown in FIGS. 4 and 5 (also in FIGS. 6 and 7 for comparison).

Though the catheter showed Young's modulus of 63 $kgf/mm^2$ under a dry condition at 25° C., sufficient stiffness for insertion to the blood vessel, it hardly softened under a wet condition at 37° C., keeping Young's modulus at 59 $kgf/mm^2$. The kink resistance of the catheter was as low as 7.0 mm under a dry condition at 25° C. and decreased to 6.8 mm after 10-minute soaking in warm water at 37° C.

Comparative Example 2

A polyurethane resin comprising 37 weight % of a soft segment made of polycaprolactone glycol having a molecular weight of 550 was extruded to form a catheter having an inner diameter of 0.68 mm and an outer diameter of 0.89 mm, which was then formed into an indwelling needle. The Young's modulus and kink resistance of this catheter were measured in the same manner as in EXAMPLE 1.

Though the catheter showed extremely high Young's modulus of 100 $kgf/mm^2$ under a dry condition at 25° C., sufficient stiffness for insertion to the blood vessel, it failed to soften sufficiently after 10-minute soaking in warm water at 37° C., exhibiting Young's modulus at 30 $kgf/mm^2$. Though the kink resistance was as high as 11.8 mm under a dry condition at 25° C. and 13.5 mm after 10-minute soaking in warm water at 37° C., this catheter failed to recover its original shape once kinked.

Comparative Example 3

A polyurethane resin comprising 46 weight % of a soft segment made of polycaprolactone glycol having a molecular weight of 550 was extruded to form a catheter having an inner diameter of 0.68 mm and an outer diameter of 0.89 mm, which was then formed into an indwelling needle. The Young's modulus and kink resistance of this catheter were measured in the same manner as in EXAMPLE 1.

This catheter was as soft as exhibiting Young's modulus of 15 kgf/mm$^2$ under a dry condition at 25° C., and further softened to Young's modulus of 1 kgf/mm$^2$ after 10-minute soaking in warm water at 37° C. Though the kink resistance of this catheter was as high as 11.1 mm under a dry condition at 25° C. and 13.5 mm after 10-minute soaking in warm water at 37° C., this catheter failed to recover its original shape once kinked under a dry condition. Also, this catheter was too soft under a wet condition at 37° C., easily collapsed.

Comparative Example 4

A polyurethane resin comprising 32 weight % of a soft segment made of polycaprolactone glycol having a molecular weight of 2000 was extruded to form a catheter having an inner diameter of 0.67 mm and an outer diameter of 0.90 mm, which was then formed into an indwelling needle. The Young's modulus and kink resistance of this catheter were measured in the same manner as in EXAMPLE 1. The Young's modulus and kink resistance of this catheter are shown in FIGS. 4 and 5 (also in FIGS. 6 and 7 for comparison).

The kink resistance was as high as 11.5 mm under a dry condition at 25° C. and 13.2 mm after 10-minute soaking in warm water at 37° C. However, this catheter did not sufficiently soften after 10-minute soaking in warm water at 37° C., exhibiting Young's modulus of 27 kgf/mm$^2$, though its Young's modulus was as large as 63 kgf/mm$^2$ under a dry condition at 25° C.

Comparative Example 5

A polyurethane resin comprising 42 weight % of a soft segment made of polycaprolactone glycol having a molecular weight of 2000 was extruded to form a catheter having an inner diameter of 0.66 mm and an outer diameter of 0.88 mm, which was then formed into an indwelling needle. The Young's modulus and kink resistance of this catheter were measured in the same manner as in EXAMPLE 1. The Young's modulus and kink resistance of this catheter are shown in FIGS. 4 and 5 (also in FIGS. 6 and 7 for comparison).

This catheter was sufficiently soft after 10-minute soaking in warm water at 37° C., exhibiting Young's modulus of 8 kgf/mm$^2$, and also soft under a dry condition at 25° C. as indicated by Young's modulus of 20 kgf/mm$^2$. However, this catheter did not exhibit large decrease percentage of dynamic storage modulus. This catheter was also poor in insatiability, making the operation of insertion difficult. The kink resistance was as poor as 9.2 mm under a dry condition at 25° C. and 10.4 mm after 10-minute soaking in warm water at 37° C.

Comparative Example 6

A catheter in a commercially available indwelling needle (Freflocath 22G, available from Nipro) was measured with respect to dynamic storage modulus both under a dry condition at 25° C. and at the elapsed time of 20 seconds and 1 minute, respectively after placed under a wet condition at 37° C. according to the above-described test method, and a decrease percentage of dynamic storage modulus was calculated at the elapsed time of 20 seconds and 1 minute, respectively. The results are shown in Table 1. The dynamic storage modulus already decreased to 75% at the elapsed time of 20 seconds after placed under a wet condition at 37° C., making the operation of insertion difficult.

Comparative Example 7

A polyurethane resin having a Shore hardness of 65 D and comprising 42 weight % of a soft segment made of polycaprolactone glycol having a molecular weight of 2000 was extruded to form a catheter having an inner diameter of 0.69 mm and an outer diameter of 0.88 mm. This catheter was measured with respect to dynamic storage modulus both under a dry condition at 25° C. and at the elapsed time of 20 seconds and 1 minute, respectively, after placed under a wet condition at 37° C. according to the above-described test method, and a decrease percentage of dynamic storage modulus was calculated at the elapsed time of 20 seconds and 1 minute, respectively. The results are shown in Table 1. The dynamic storage modulus was as small as 59% at the elapsed time of 1 minute after placed under a wet condition at 37° C.

TABLE 1

| | Dynamic Storage Modulus | | |
|---|---|---|---|
| | Dry Condition | Decrease Percentage (%) | |
| No. | at 25° C. (GPa) | After 20 seconds | After 1 minute |
| EXAMPLE 1 | 1.4 | 54 | 74 |
| EXAMPLE 5 | 1.3 | 52 | 69 |
| EXAMPLE 9 | 1.0 | 45 | 69 |
| EXAMPLE 11 | 1.3 | 55 | 68 |
| COMP. EX. 6 | 1.2 | 75 | 83 |
| COMP. EX. 7 | 0.81 | 39 | 59 |

As mentioned above, the indwelling catheter of the present invention has as large dynamic storage modulus as 1 GPa or more under a dry condition at 25° C., and a decrease percentage of its dynamic storage modulus when changed from a dry condition at 25° C. to a wet condition at 37° C. is less than 60% at the elapsed time of 20 seconds and 60% or more at the elapsed time of 1 minute. Therefore, the indwelling catheter of the present invention exhibits sufficient stiffness at the time of insertion and fully softens after being left in the blood vessel. The indwelling catheter of the present invention exhibits as high kink resistance as 10 mm or more both under a dry condition at 25° C. and under a wet condition at 37° C., safely keeping a flow passage in the catheter after indwelling. Unlike the conventional catheters, the indwelling catheter of the present invention is sufficiently stiff at the time of insertion and becomes soft at a proper speed after indwelling without losing the kink resistance, thereby avoiding the blood vessel from being damaged.

What is claimed is:

1. An indwelling catheter made of a blend of a plurality of polyurethane resins, wherein said indwelling catheter has a dynamic storage modulus of 1 GPa or more under a dry condition at 25° C. and shows decrease in dynamic storage modulus when changed from a dry condition at 25° C. to a wet condition at 37° C., a decrease percentage $E_p$ of said dynamic storage modulus, which is represented by the following equation:

$$E_p = [(E_0 - E_t)/(E_0 - E_{30})] \times 100\%,$$

wherein $E_0$ is a dynamic storage modulus under the dry condition at 25° C., $E_{30}$ is a dynamic storage modulus at the elapsed time of 30 minutes after placed under the wet condition at 37° C., and $E_t$ is a dynamic storage modulus at the elapsed time of t after placed under the wet condition at 37° C., being less than 60% at the elapsed time of 20 seconds after placed under the wet condition at 37° C. and 60% or more at the elapsed time of 1 minute after placed under the wet condition at 37° C.

2. The indwelling catheter according to claim 1, wherein said indwelling catheter is made of a blend of a plurality of polyurethane resins each comprising at least one diisocyanate, at least one diol chain extender and at least one polyglycol, said polyglycols having different molecular weights.

3. The indwelling catheter according to claim 1, wherein said plurality of polyurethane resins comprise a first polyurethane resin containing 20–70 weight % of polyglycol having a molecular weight of 500–1500 and a second polyurethane resin containing 20–70 weight % of polyglycol having a molecular weight of 1500–3000, the difference in molecular weight between the polyglycol in said first polyurethane resin and the polyglycol in said second polyurethane resin being 500 or more.

4. The indwelling catheter according to claim 3, wherein a weight ratio of said first polyurethane resin to said second polyurethane resin is from 8:2 to 2:8.

5. The indwelling catheter according to claim 1, wherein each of said polyurethane resins is a reaction product of 4,4'-diphenylmethane diisocyanate, 1,4-butanediol and polycaprolactone glycol and has a Shore hardness of 60 D or more.

6. The indwelling catheter according to claim 3, wherein each of said polyurethane resins is a reaction product of 4,4'-diphenylmethane diisocyanate, 1,4-butanediol and polycaprolactone glycol and has a Shore hardness of 60 D or more.

7. The indwelling catheter according to claim 1, having kink resistance of 10 mm or more both under a dry condition at 25° C. and a wet condition at 37° C.

8. The indwelling catheter according to claim 1, having a Young's modulus of 50 kgf/mm$^2$ or more under a dry condition at 25° C., which reduces to 25 kgf/mm$^2$ or less within 5 minutes when placed under a wet condition at 37° C.

9. An indwelling catheter made of a blend of a plurality of polyurethane resins each comprising at least one polyglycol, said polyglycols having different molecular weights, wherein said plurality of polyurethane resins comprise a first polyurethane resin containing 20–70 weight % of polyglycol having a molecular weight of 500–1500 and a second polyurethane resin containing 20–70 weight % of polyglycol having a molecular weight of 1500–3000, the difference in molecular weight between the polyglycol in said first polyurethane resin and the polyglycol in said second polyurethane resin being 500 or more.

10. The indwelling catheter according to claim 9, wherein a weight ratio of said first polyurethane resin to said second polyurethane resin is from 8:2 to 2:8.

11. The indwelling catheter according to claim 9, wherein each of said polyurethane resins is a reaction product of 4,4'-diphenylmethane diisocyanate, 1,4-butanediol and polycaprolactone glycol and has a Shore hardness of 60 D or more.

12. The indwelling catheter according to claim 9, having kink resistance of 10 mm or more both under a dry condition at 25° C. and a wet condition at 37° C.

13. The indwelling catheter according to claim 9, having a Young's modulus of 50 kgf/mm' or more under a dry condition at 25° C., which reduces to 25 kgf/mm' or less within 5 minutes when placed under a wet condition at 37° C.

14. The indwelling catheter according to claim 9, wherein each of said polyurethane resins comprises a diisocyanate, a diol chain extender and a plurality of polyglycols having different molecular weights.

15. An indwelling catheter made of a polyurethane resin containing a plurality of polyglycols having different molecular weights, wherein said indwelling catheter has a dynamic storage modulus of 1 GPa or more under a dry condition at 25° and shows decrease in dynamic storage modulus when changed from a dry condition at 25° to a wet condition at 37°, a decrease percentage Ep of said dynamic storage modulus, which is represented by the following equation:

$$E_p = [(E_0 E_t / (E_0 - E_{30})] \times 100\%,$$

wherein $E_0$ is a dynamic storage modulus under the dry condition at 25° C., $E_{30}$ is a dynamic storage modulus at the elapsed time of 30 minutes after placed under the wet condition at 37° C., and $E_t$ is a dynamic storage modulus at the elapsed time of t after placed under the wet condition at 37° C., being less than 60% at the elapsed time of 20 seconds after placed under the wet condition at 37° C. and 60% or more at the elapsed time of 1 minute after placed under the wet condition at 37° C.

16. The indwelling catheter according to claim 15, wherein said polyurethane resin comprises a diisocyanate, a diol chain extender and the plurality of polyglycols having different molecular weights.

17. The indwelling catheter according to claim 15, wherein said plurality of polyglycols comprise a first polyglycol having a molecular weight of 500–1500 and a second polyglycol having a molecular weight of 1500–3000, the difference in molecular weight between said first polyglycol and said second polyglycol being 500 or more.

18. The indwelling catheter according to claim 17, wherein a weight ratio of said first polyglycol to said second polyglycol is from 8:2 to 2:8.

19. The indwelling catheter according to claim 15, wherein said polyurethane resin is a reaction product of 4,4'diphenylmethane diisocyanate, 1,4-butanediol and a plurality of polycaprolactone glycols having different molecular weights and has a Shore hardness of 60 D or more.

20. The indwelling catheter according to claim 17, wherein said polyurethane resin is a reaction product of 4,4'-diphenylmethane diisocyanate, 1,4-butanediol and a plurality of polycaprolactone glycols having different molecular weights and has a Shore hardness of 60 D or more.

21. The indwelling catheter according to claim 15, having kink resistance of 10 mm or more both under a dry condition at 25° C. and a wet condition at 37° C.

22. The indwelling catheter according to claim 15, having a Young's modulus of 50 kgf/mm$^2$ or more under a dry condition at 25° C., which reduces to 25 kgf/mm$^2$ or less within 5 minutes when placed under a wet condition at 37° C.

23. An indwelling catheter made of a polyurethane resin containing a plurality of polyglycols having different molecular weights, wherein said polyurethane resin comprises a diisocyanate, a diol chain extender and the plurality of polyglycols having different molecular weights, wherein said plurality of polyglycols comprise a first polyglycol having a molecular weight of 500–1500 and a second polyglycol having a molecular weight of 1500–3000, the difference in molecular weight between said first polyglycol and said second polyglycol being 500 or more.

24. The indwelling catheter according to claim 23, wherein a weight ratio of said first polyglycol to said second polyglycol is from 8:2 to 2:8.

25. The indwelling catheter according to claim 23, wherein said polyurethane resin is a reaction product of 4,4'-diphenylmethane diisocyanate, 1,4-butanediol and a plurality of polycaprolactone glycols having different molecular weights and has a Shore hardness of 60 D or more.

26. The indwelling catheter according to claim 23, wherein said polyurethane resin is a reaction product of 4,4'-diphenylmethane diisocyanate, 1,4-butanediol and a plurality of polycaprolactone glycols having different molecular weights and has a Shore hardness of 60 D or more.

27. The indwelling catheter according to claim 23, having kink resistance of 10 mm or more both under a dry condition at 25° C. and a wet condition at 37° C.

28. The indwelling catheter according to claim 23, having a Young's modulus of 50 kgf/mm$^2$ or more under a dry condition at 25° C., which reduces to 25 kgf/mm$^2$ or less within 5 minutes when placed under a wet condition at 37° C.

* * * * *